US00PP14531P29

(12) United States Plant Patent

Warren et al.

(10) Patent No.: US PP14,531 P2
(45) Date of Patent: Feb. 10, 2004

(54) CALLA LILY PLANT NAMED 'PINK POT'

(50) Latin Name: *Zantedeschia spp.*
Varietal Denomination: Pink Pot

(75) Inventors: Andrew G. F. Warren, Tauranga (NL); Jacobus J. P. Spaans, Tauranga (NL)

(73) Assignee: Bloomz Limited, Tauranga (NZ)

( * ) Notice: Subject to any disclaimer, the term of this patent is extended or adjusted under 35 U.S.C. 154(b) by 0 days.

(21) Appl. No.: 10/382,759

(22) Filed: Mar. 6, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Susan B. McCormick
(74) *Attorney, Agent, or Firm*—Jondle & Associates, PC

(57) ABSTRACT

A calla lily potted plant particularly distinguished by pink spathe and lightly maculated leaves.

3 Drawing Sheets

Genus and species: Zantedeschia spp.
Variety denomination: 'Pink Pot'.

BACKGROUND OF THE NEW PLANT

The present invention comprises a new and distinct cultivar of calla lily, botanically known as Zantedeschia spp, and hereinafter referred to by the cultivar name 'Pink Pot'. The new cultivar is asexually reproduced from vegetative cuttings and tissue culture resulting from the cross of the seed parent that is a pink seedling, a proprietary line that is unnamed and unpatented×'Pink Persuasion' (patent status unknown).

'Pink Pot' is a product of a planned breeding program intended to create new calla lily pot plants with pink spathes.

The new cultivar was created in 1998 in Tauranga New Zealand and has been asexually reproduced repeatedly by vegetative cuttings and tissue culture in New Zealand over a 3 year period. The present invention has been found to retain its distinctive characteristics through successive propagations; and this novelty is firmly fixed.

DESCRIPTION OF PHOTOGRAPH

This new calla lily plant is illustrated by the accompanying photographs which show blooms, buds, and foliage of the plant in full color, the colors shown being as true as can be reasonably obtained by conventional photographic procedures.

DESCRIPTION OF THE NEW CULTIVAR

Figure 1:
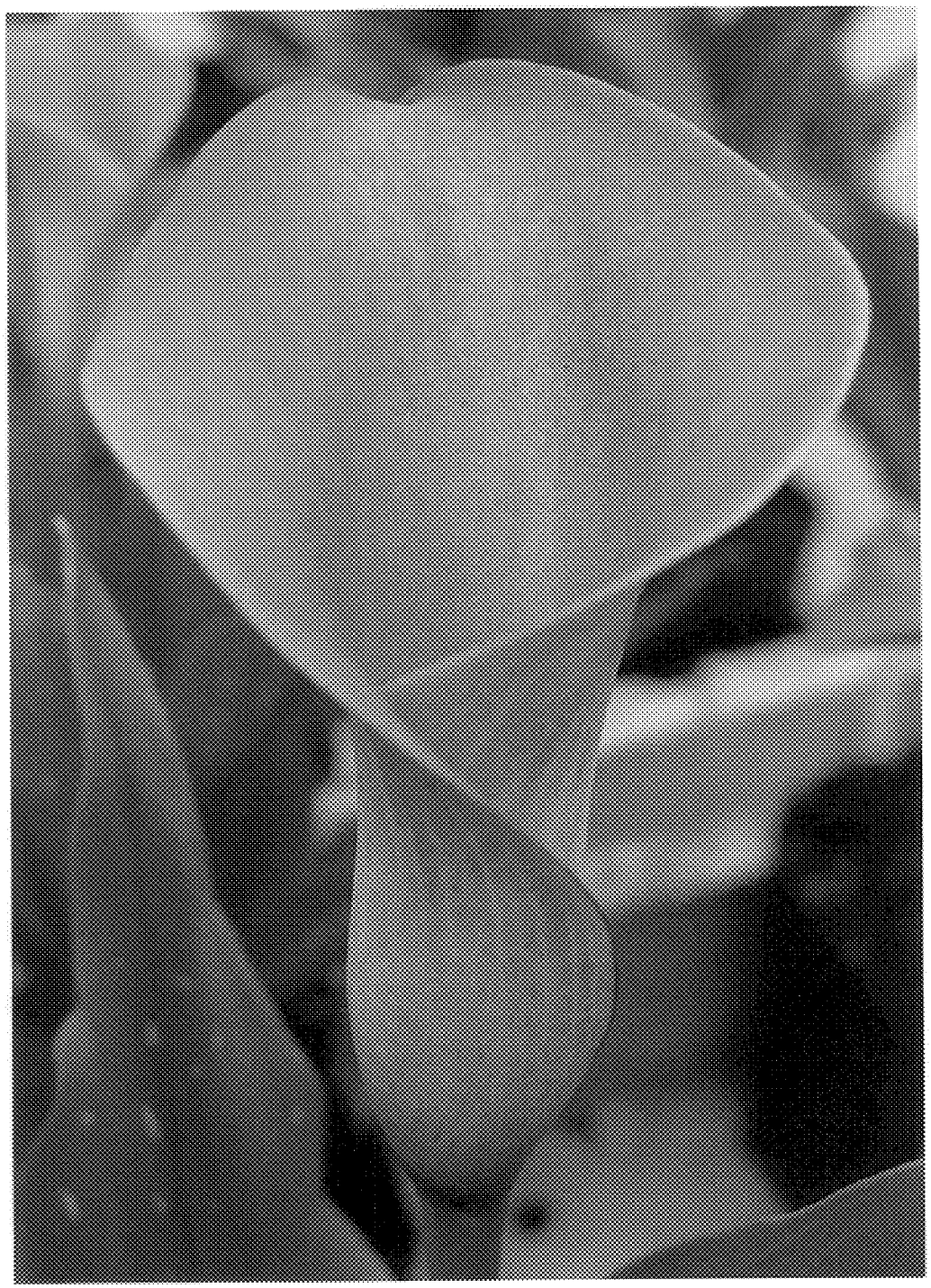
FIG. 1 shows the mature inflorescence.
Figure 2:
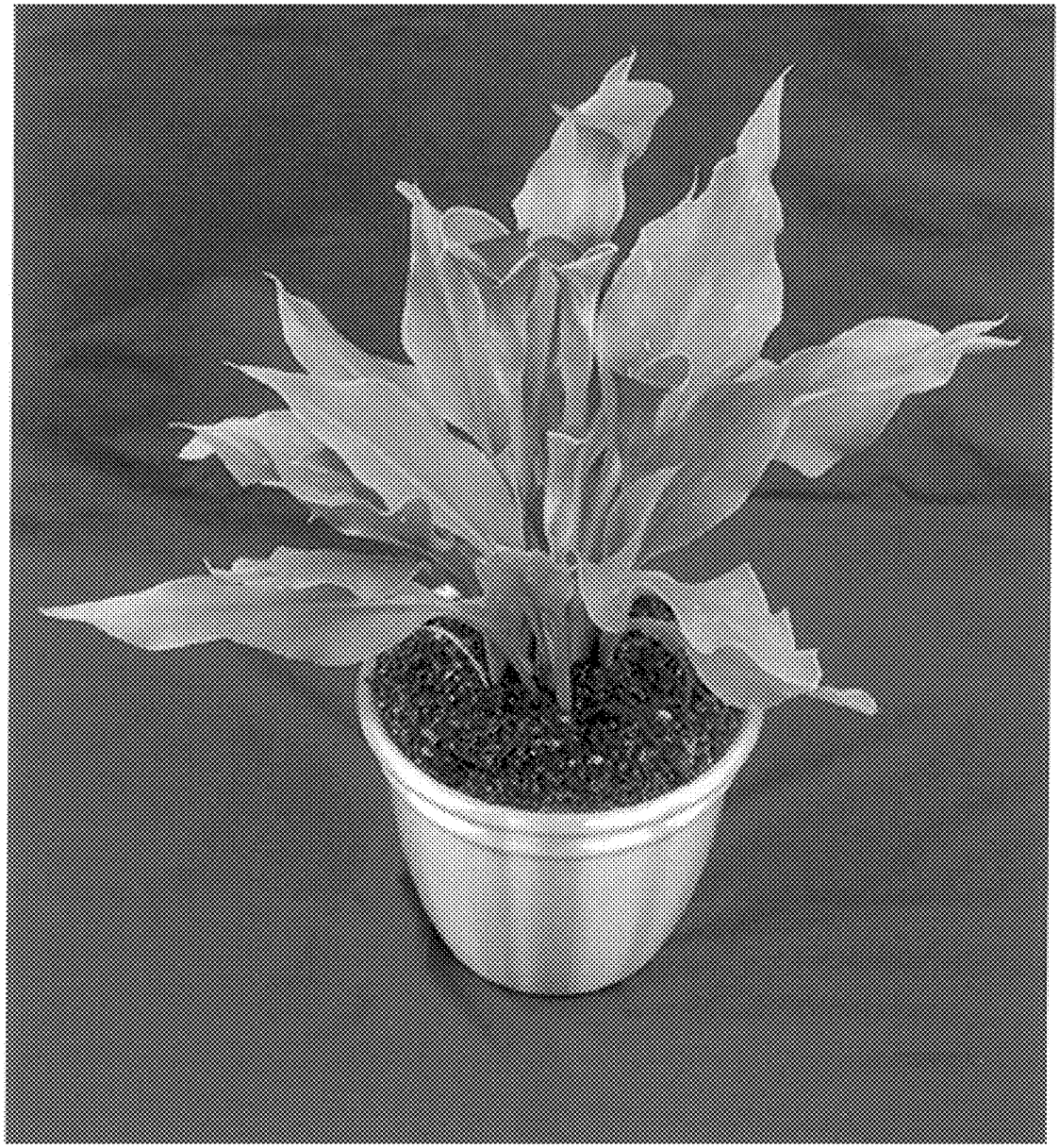
FIG. 2 shows the overall plant habit.
Figure 3:
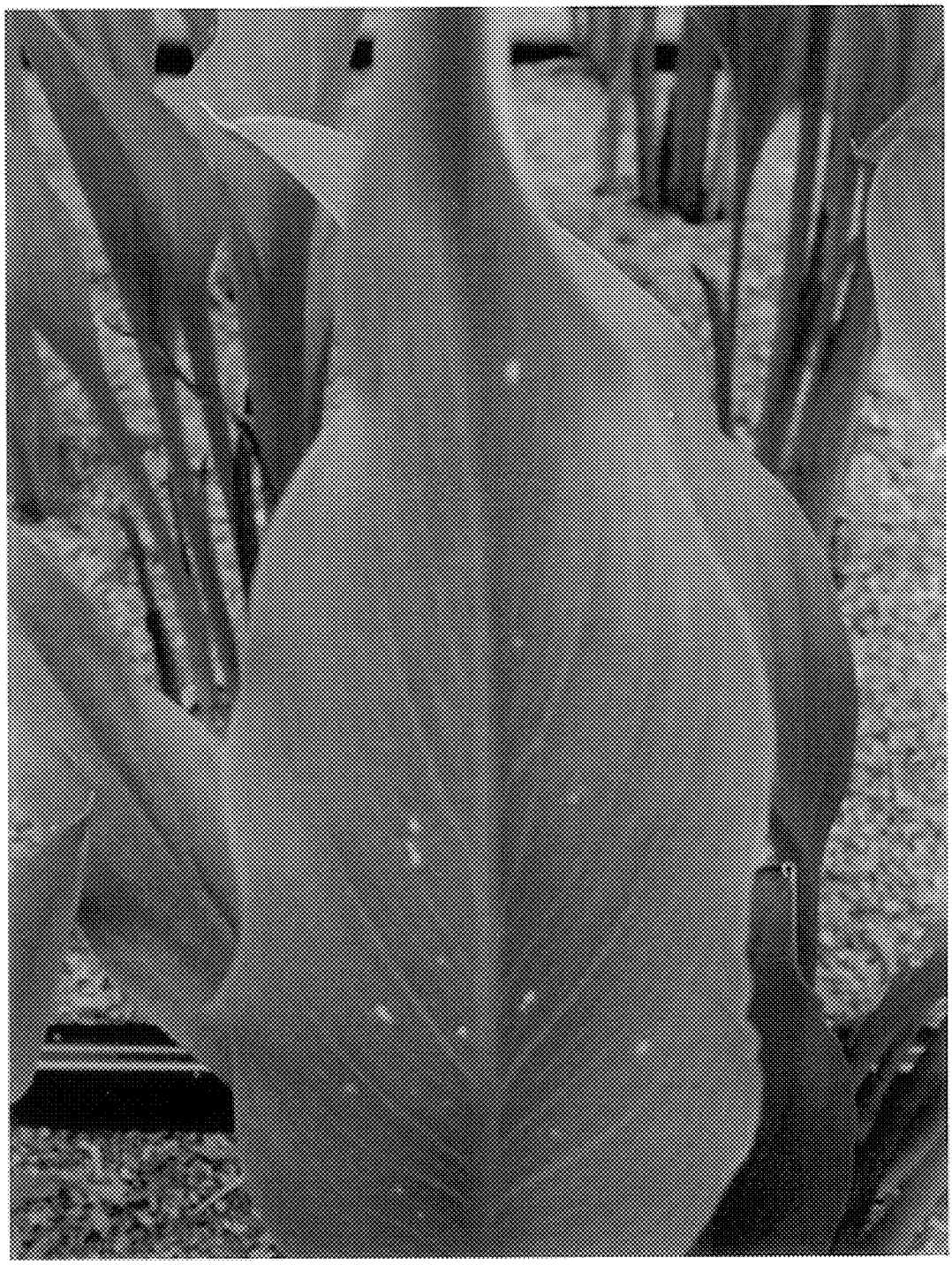
FIG. 3 shows the leaves.

The following detailed descriptions set forth the distinctive characteristics of 'Pink Pot'. The data which defines these characteristics were collected from asexual reproductions carried out in New Zealand. The plant history was taken on 2 year old plants based on a 4 cm diameter tuber under New Zealand Spring conditions. Color references are primarily to The R.H.S Colour Chart of The Royal Horticultural Society of London (R.H.S.).

THE PLANT

Classification:
- *Botanical.*—Zantedeschia spp.
- *Commercial.*—Calla lily.
- *Variety.*—'Pink Pot'.

Size:
- *Form.*—Erect.
- *Height of the leaf canopy above the soil.*—20–30 cm.
- *Height of top of inflorescence above the soil.*—30–40 cm.
- *Diameter.*—15–25 cm.
- *Number of inflorescence per tuber size.*—Tuber diameter 3 cm 4–6. Tuber diameter 4 cm 5–8. Tuber diameter 5 cm 8+.

Branches:
- *Character.*—Strong.
- *Color.*—Upper is green RHS 144B; lower is green RHS 144C; base is white RHS 155C.
- *Average number.*—3–4.

Leaves:
- *Size.*—Width 6–10 cm; length 15–25 cm.
- *Shape.*—Ovate.
- *Color.*—Upper is green RHS 137A; lower is green RHS 137B.
- *Maculation* (*leaf spots*).—Low density; white RHS 155C.
- *Apex.*—Acute to apiculate.
- *Margin.*—Moderately wavy.
- *Margin color.*—Green RHS 137A.
- *Veins.*—Pinnate.
- *Surface quality.*—Leathery.

Petiole (leaf stalk):
- *Length.*—10–15 cm.
- *Color.*—Base is Green RHS 144C; upper is green RHS 144B.

Roots:
- *Color.*—White.
- *Branching.*—Not branched, attached to the top of the tuber at the apices.
- *Disease resistance.*—No susceptibility noted to date.
- *Pest resistance.*—No susceptibility noted to date.

THE INFLORESCENCE

Spathe (flower body):

*Size.*—Length 8–10 cm; width 4.5–5.5 cm.

*Color.*—Upper is pink RHS 74C; lower is pink RHS 66D.

*Veins.*—Present, pink purple RHS 66C.

*Shape.*—Fluted.

Spadix (reproductive organs):

*Size.*—Length 3–4 cm; diameter 0.3–0.5 cm.

*Color.*—Base is yellow RHS 10C; Upper is yellow RHS 10B.

*Position relative to spathe.*—Upright.

Peduncle (flower stem):

*Size.*—20–30 cm.

*Color.*—Green RHS 144B; upper is Green RHS 144C.

Reproductive organs:

*Location of female organs.*—Basal position of the spadix.

*Location of male organs.*—Upper position of the spadix Perianth (the floral envelope — calyx and corolla) Conspicuous.

*Stamens.*—Not visible before pollen release.

*Pistil.*—30'per spadix; yellow-green RHS 150C.

Miscellaneous:

*Time to produce a finished flowering plant.*—6–10 weeks.

*Lastingness.*—2–3 weeks.

*Fragrance.*—None.

*Fruit.*—None.

*Production.*—30–40 berries.

*Color.*—Predominantly lime green RHS 150C with purple markings RHS 78A.

COMPARISON WITH KNOWN CULTIVARS

When the instant plant is compared to 'Ruby Light Red' (patent status unknown) the 'Pink Pot' foliage has a low density of maculation and the shape of the leaves are ovate. Additionally the flower color is more intense than 'Ruby Light Red'.

I claim:

1. A new and distinct cultivar of calla lily plant as shown and described herein.

* * * * *